US012044271B2

(12) United States Patent
Hsu et al.

(10) Patent No.: US 12,044,271 B2
(45) Date of Patent: Jul. 23, 2024

(54) STIFFNESS GAIN MECHANISM FOR MAGNETIC SUSPENSION BEARING, MAGNETIC SUSPENSION BEARING, AND BLOOD PUMP

(71) Applicant: Magassist, Inc., Jiangsu (CN)

(72) Inventors: Chiahao Hsu, Jiangsu (CN); Polin Hsu, Jiangsu (CN); Ifan Yen, Jiangsu (CN); Thomas George Logan, Jiangsu (CN)

(73) Assignee: Magassist, Inc., Jiangsu (CN)

( * ) Notice: Subject to any disclaimer, the term of this patent is extended or adjusted under 35 U.S.C. 154(b) by 154 days.

(21) Appl. No.: 17/429,017

(22) PCT Filed: Jan. 20, 2020

(86) PCT No.: PCT/CN2020/073208
§ 371 (c)(1),
(2) Date: Aug. 6, 2021

(87) PCT Pub. No.: WO2020/164371
PCT Pub. Date: Aug. 20, 2020

(65) Prior Publication Data
US 2022/0106981 A1 Apr. 7, 2022

(30) Foreign Application Priority Data

Feb. 14, 2019 (CN) .......................... 201910113382.1

(51) Int. Cl.
*F16C 32/04* (2006.01)
*A61M 60/178* (2021.01)
(Continued)

(52) U.S. Cl.
CPC ....... *F16C 32/0436* (2013.01); *A61M 60/178* (2021.01); *A61M 60/216* (2021.01);
(Continued)

(58) Field of Classification Search
CPC .............. F16C 32/0436; F16C 32/0446; F16C 32/0451; F16C 2316/18; F16C 32/0412;
(Continued)

(56) References Cited

U.S. PATENT DOCUMENTS 5,196,748 A 3/1993 Rigney
5,521,448 A 5/1996 Tecza et al.
(Continued)

FOREIGN PATENT DOCUMENTS

CN 1687606 A 10/2005
CN 101297123 A 10/2008
(Continued)

OTHER PUBLICATIONS

CN107261231A English translation (Year: 2023).*
CN102155492A English translation (Year: 2023).*
Search Report dated Dec. 2, 2021 cited in corresponding Russian Application No. 2021122681; 2 pages.

*Primary Examiner* — Christopher M Koehler
*Assistant Examiner* — Viswanathan Subramanian
(74) *Attorney, Agent, or Firm* — Flaster Greenberg P.C.

(57) ABSTRACT

The present disclosure relates to a stiffness enhancing mechanism for a magnetic suspension bearing, a magnetic suspension bearing including the stiffness enhancing mechanism, and a blood pump. The magnetic suspension bearing comprises a stator with stator teeth and a rotor disposed within the stator. The stiffness enhancing mechanism comprises: a rotor permanent magnet, a stator permanent magnet, and an axial driving body. The rotor permanent magnet and the rotor of the magnetic suspension bearing form a rotor assembly, which has an asymmetric structure with respect to the main plane (P) of the rotor. The stiffness enhancing mechanism is configured such that the stator permanent magnet generates a radial attractive force to the rotor permanent magnet, and the axial driving body generates an axial repulsive force to the rotor permanent magnet, (Continued)

wherein the magnitude of the axial repulsive force is variable with a change of an axial distance between the axial driving body and the rotor permanent magnet. The stiffness enhancing mechanism can increase the torsional stiffness of the rotor of the magnetic suspension bearing and facilitate the miniaturization of the magnetic suspension bearing.

18 Claims, 5 Drawing Sheets

(51) Int. Cl.
*A61M 60/216* (2021.01)
*A61M 60/422* (2021.01)
*A61M 60/822* (2021.01)

(52) U.S. Cl.
CPC ........ *A61M 60/422* (2021.01); *A61M 60/822* (2021.01); *F16C 32/0446* (2013.01); *F16C 32/0451* (2013.01); *F16C 2316/18* (2013.01)

(58) Field of Classification Search
CPC .............. F16C 32/0427; F16C 32/0442; F16C 32/0465; F16C 32/0468; F16C 32/0478; F16C 32/0485; F16C 32/0459; F16C 32/044; A61M 60/178; A61M 60/216; A61M 60/422; A61M 60/822; A61M 60/104
See application file for complete search history.

(56) References Cited

U.S. PATENT DOCUMENTS

| | | | |
|---|---|---|---|
| 5,686,772 A * | 11/1997 | Delamare | ........... F16C 32/0408 310/90 |
| 6,181,040 B1 | 1/2001 | Schob | |
| 2002/0074881 A1 | 6/2002 | Imlach | |
| 2002/0074884 A1 | 6/2002 | Fuller | |
| 2009/0315421 A1 * | 12/2009 | Onuma | ................. F16C 32/048 310/90.5 |
| 2016/0123387 A1 | 5/2016 | Post | |

FOREIGN PATENT DOCUMENTS

| | | | | |
|---|---|---|---|---|
| CN | 102155492 A | * | 8/2011 | .......... F16C 32/0465 |
| CN | 102247628 A | | 11/2011 | |
| CN | 102322481 A | | 1/2012 | |
| CN | 102434587 A | | 5/2012 | |
| CN | 102155492 B | | 12/2012 | |
| CN | 107261231 A | | 10/2017 | |
| CN | 108679084 A | | 10/2018 | |
| EP | 0664410 A1 | | 7/1995 | |
| EP | 1942282 A | | 7/2008 | |
| EP | 2372160 A1 | | 10/2011 | |
| JP | 2005016677 A | | 1/2005 | |
| RU | 135378 U1 | | 12/2013 | |
| WO | 2009140022 A2 | | 11/2009 | |

* cited by examiner

STIFFNESS GAIN MECHANISM FOR MAGNETIC SUSPENSION BEARING, MAGNETIC SUSPENSION BEARING, AND BLOOD PUMP

CROSS-REFERENCE TO RELATED APPLICATIONS

This application is the 371 U.S. national phase of PCT international patent application number PCT/CN2020/073208, filed Jan. 20, 2020, which claims priority to Chinese patent application number 201910113382.1, filed on Feb. 14, 2019. The disclosure of each aforementioned application is incorporated by reference herein in its entirety. Specifically, PCT international patent application number PCT/CN2020/073208 is incorporated by reference herein in its entirety. And, Chinese patent application number 201910113382.1 is incorporated by reference herein in its entirety.

TECHNICAL FIELD

The present disclosure generally relates to the field of medical instruments. More specifically, the present disclosure relates to a stiffness enhancing mechanism for a magnetic suspension bearing, a magnetic suspension bearing including the stiffness enhancing mechanism, and a blood pump.

BACKGROUND ART

In the case where a heart loses its blood pumping function (such as arrested heart surgery, acute cardiogenic shock, etc.), a blood pump may be used to replace the heart to assist in maintaining the blood circulation of human body. The blood pump may be an implantable blood pump that is implantable into a patient's body to maintain the blood circulation of human body temporarily or permanently, or an extracorporeal blood pump that is usable outside the human body.

It is advantageous to use a magnetic suspension bearing in the blood pump. The magnetic suspension bearing, which functions with magnetic force, typically includes a rotor that is rotatable about a specific axis of rotation, and a magnetic force providing mechanism that provides magnetic force to suspend the rotor. According to the difference in the magnetic force providing mechanism, the magnetic suspension bearing may be classified as an active magnetic suspension bearing or a passive magnetic suspension bearing, wherein the magnetic force providing mechanism of the active magnetic suspension bearing may be an electromagnet, whereas the magnetic force providing mechanism of the passive magnetic suspension bearing may be a permanent magnet or a ferromagnetic material. The active magnetic suspension bearing usually further includes a displacement sensor, and a controller that controls magnitude of current through the electromagnet based on a signal from the displacement sensor to regulate the suspension electromagnetic force. In operation, locations of the rotor that relate to active magnetic suspension degrees of freedom are firstly provided to the controller by the displacement sensor, and then the controller provides a specific current to the electromagnet via a corresponding control algorithm (PID, PI, PD control, etc.) to generate a controlled suspension electromagnetic force. The passive magnetic suspension bearing generates attractive force or repulsive force based on interactions between two or more permanent magnets or between a permanent magnet and a ferromagnetic material to suspend the rotor at a balanced position.

Compared with a traditional bearing like a mechanical bearing, the rotor of the magnetic suspension bearing has no physical contact with other components (such as the magnetic force providing mechanism, etc.), and the rotor may be spaced apart from other components by a large gap, rendering significant advantageous of the magnetic suspension bearing. On one hand, mechanical wear of respective components of the magnetic suspension bearing can be eliminated due to the absence of physical contact; on the other hand, the large gap allows a fluid flowing through the gap to suffer less shear stress, which, in the case where the fluid is blood, can help to reduce damages to the blood cells and accordingly can improve blood compatibility.

FIG. 1 is a schematic view of an active magnetic suspension bearing 10. The active magnetic suspension bearing 10 includes: a rotor 101 that is rotatable about an axis of rotation A; an electromagnet 102 that provides electromagnetic force to suspend the rotor 101, wherein a gap or an airgap G1 is present between the rotor 101 and the electromagnet 102; a displacement sensor 103 for detecting the displacement of the rotor 101 relative to the electromagnet 102; and a controller 104, which controls magnitude of current through the electromagnet 102 based on signals from the displacement sensor 103 to regulate the suspension electromagnetic force.

In the active magnetic suspension bearing 10 shown in FIG. 1, the electromagnet 102 provides radial electromagnetic force (i.e., the electromagnetic force in an X-Y plane) to the rotor 101 to ensure that the rotor 101 is stably suspended in the radial direction. However, the active magnetic suspension bearing 10 shown in FIG. 1 is prone to generating torsional movement about an X-axis or a Y-axis. In other words, the active magnetic suspension bearing 10 shown in FIG. 1 has a degree of freedom of torsion (that is, the degree of freedom of rotation with the X-axis or Y-axis as the axis of rotation), and alternatively speaking, the active magnetic suspension bearing 10 shown in FIG. 1 has a low torsional stiffness, which is undesirable. It is desirable that the magnetic suspension bearing has a torsional stiffness as high as possible so that the magnetic suspension bearing has no or rare torsional movement.

In order to solve above mentioned problem, a known method is to combine multiple layers of permanent magnets and ferromagnetic materials to form a sandwich-like structure, so that multiple parallel push and pull forces are formed on a plane perpendicular to the axis of rotation A (i.e., the X-Y plane shown in FIG. 1) to thereby increase the torsional stiffness and improve the torsional stability. However, such sandwich structure has some drawbacks. On one hand, the strength of a permanent magnet is proportional to its volume: the larger the volume, the higher the strength of the permanent magnet; on the other hand, the smaller the volume of the permanent magnet, the more obvious the magnetization marginal effect of the permanent magnet. That is to say, the magnetic field intensity generated by a permanent magnet formed of a plurality of small permanent magnets is not equal to but less than the magnetic field intensity generated by a single permanent magnet of the same volume. Therefore, when above-mentioned sandwich structure formed of a plurality of permanent magnets is used, in order to reach a desired magnetic field intensity as that generated by a single permanent magnet, it needs to increase the volume of each small permanent magnet, which may necessarily lead to an increase in the total volume of the magnetic suspension bearing, thus limiting its scope of application. In many current applications, there are usually strict limitations for the volume of the rotor, and it is generally desired that the rotor can be miniaturized. For example, in the application in the blood pump, the gap or airgap in the magnetic suspension bearing is generally shared with a secondary flow path of the blood pump. When the blood flows in a secondary flow path narrower than a main flow path, it may suffer shear stress for a long period, thus causing damage to blood cells. Therefore, miniaturizing the rotor so as to shorten the length of the secondary flow path as much as possible is very important for the blood compatibility of the blood pump. In this kind of application, the miniaturization of the rotor is an important optimization target; however, the sandwich structure runs counter to this target.

Therefore, there is a demand to further modify the current magnetic suspension bearings.

CONTENT OF THE INVENTION

The above-mentioned problems and other problems will be overcome and additional advantages are to be achieved by exemplary embodiments of the present disclosure.

According to a first aspect of exemplary embodiments of the present disclosure, a stiffness enhancing mechanism for a magnetic suspension bearing is provided. The magnetic suspension bearing may include a stator and a rotor disposed within the stator, wherein the stator includes stator teeth. The stiffness enhancing mechanism may comprise: a rotor permanent magnet arranged on a side of the rotor with the rotor permanent magnet being parallel to a main plane of the rotor and abutting against the rotor, wherein the main plane of the rotor is a symmetrical plane of the rotor in a radial direction; a stator permanent magnet arranged on a side of the stator teeth of the stator with the stator permanent magnet being parallel to the main plane of the rotor and abutting against the stator teeth of the stator, wherein the side where the stator permanent magnet is located is the same as the side where the rotor permanent magnet is located, and the stator permanent magnet is spaced apart from the rotor permanent magnet by a certain distance in the radial direction; and an axial driving body arranged to face the rotor permanent magnet and be spaced apart from the rotor permanent magnet by a certain distance in an axial direction. The rotor permanent magnet and the rotor form a rotor assembly, which has an asymmetric structure with respect to the main plane of the rotor. The stiffness enhancing mechanism is configured such that the stator permanent magnet generates a radial attractive force to the rotor permanent magnet, and the axial driving body generates an axial repulsive force to the rotor permanent magnet, wherein the magnitude of the axial repulsive force is variable with a change of an axial distance between the axial driving body and the rotor permanent magnet.

According to an exemplary embodiment of the present disclosure, each of the rotor permanent magnet and the stator permanent magnet may have a mono-magnetization direction.

According to an exemplary embodiment of the present disclosure, the rotor permanent magnet and/or the stator permanent magnet may have an axial magnetization direction.

According to an exemplary embodiment of the present disclosure, the rotor permanent magnet and/or the stator permanent magnet may have a radial magnetization direction.

According to an exemplary embodiment of the present disclosure, each of the rotor permanent magnet and the stator permanent magnet may be of an integral structure in a circular shape.

According to an exemplary embodiment of the present disclosure, the rotor permanent magnet and/or the stator permanent magnet may be composed of a plurality of discrete permanent magnets spaced apart from each other in a circumferential direction.

According to an exemplary embodiment of the present disclosure, the axial driving body may be configured to be stationary.

According to an exemplary embodiment of the present disclosure, the axial driving body may be a permanent magnet.

According to an exemplary embodiment of the present disclosure, the axial driving body may be a permanent magnet having an integral structure in a circular shape.

According to an exemplary embodiment of the present disclosure, the axial driving body may be composed of a plurality of discrete permanent magnets spaced apart from each other in a circumferential direction.

According to an exemplary embodiment of the present disclosure, the axial driving body may be an electromagnet or an air coil.

According to an exemplary embodiment of the present disclosure, the axial driving body may be composed of a plurality of electromagnets or air coils spaced apart from each other in a circumferential direction.

According to an exemplary embodiment of the present disclosure, the stiffness enhancing mechanism may further include a controller or a control circuit, which can separately vary magnitude of current flowing through each electromagnet or air coil and accordingly can separately change the magnitude of the axial repulsive force generated by the corresponding one or more electromagnets or air coils to the rotor permanent magnet.

According to an exemplary embodiment of the present disclosure, when a torsional movement about the radial direction occurs to the rotor, the controller or the control circuit of the stiffness enhancing mechanism reduces the current flowing through one or more electromagnets or air coils corresponding to an end of the rotor away from the axial driving body and meanwhile increases the current flowing through one or more electromagnets or air coils corresponding to the other end of the rotor close to the axial driving body.

According to an exemplary embodiment of the present disclosure, the controller or control circuit of the stiffness enhancing mechanism is also capable of separately changing direction of current flowing through each electromagnet or air coil. When a torsional movement about the radial direction occurs to the rotor, the controller or control circuit of the stiffness enhancing mechanism changes the direction of current flowing through one or more electromagnets or air coils corresponding to an end of the rotor away from the axial driving body, so as to change the axial repulsive force generated by the one or more electromagnets or air coils to the rotor permanent magnet into an axial attractive force.

According to a second aspect of exemplary embodiments of the present disclosure, there is provided a magnetic suspension bearing, which includes the stiffness enhancing mechanism according to the exemplary embodiments of the present disclosure.

According to an exemplary embodiment of the present disclosure, the stator of the magnetic suspension bearing may comprise a plurality of stator teeth spaced apart from each other in a circumferential direction, and each of the stator teeth is provided with a magnetic suspension coil for suspending the rotor of the magnetic suspension bearing and controlling the movement of the rotor in the radial direction.

According to an exemplary embodiment of the present disclosure, each of the stator teeth may include a horizontal portion and a vertical portion to assume an inverted "L" shape, wherein the horizontal portion of each stator tooth and the rotor are located at substantially same heights with a gap existing between the horizontal portion of the stator tooth and the rotor, the magnetic suspension coil is wound on the vertical portion of the stator tooth, and a magnetic flux generated by the magnetic suspension coil is capable of passing through the horizontal portion of the stator tooth, through the gap between the horizontal portion of the stator tooth and the rotor, and through the rotor.

According to an exemplary embodiment of the present disclosure, each of the stator teeth may extend from a stator body towards the center in the radial direction to assume a linear shape, wherein each stator tooth and the rotor are located at substantially same heights with a gap existing between the stator tooth and the rotor, the magnetic suspension coil is wound on the stator tooth, and the magnetic flux generated by the magnetic suspension coil is capable of passing through the stator tooth, through the gap between the stator tooth and the rotor, and through the rotor.

According to an exemplary embodiment of the present disclosure, the magnetic suspension bearing may further comprise a displacement sensor and a controller, wherein the displacement sensor is used to measure a displacement of the rotor in the radial direction and send a displacement signal to the controller of the magnetic suspension bearing, and the controller of the magnetic suspension bearing separately changes magnitude and/or direction of current flowing through corresponding one or more magnetic suspension coils based on the displacement signal to thereby control movement of the rotor in the radial direction.

According to an exemplary embodiment of the present disclosure, the stator permanent magnet of the stiffness enhancing mechanism may be abutted against a surface of the stator.

According to an exemplary embodiment of the present disclosure, the magnetic suspension bearing may further comprise a support structure for supporting the axial driving body of the stiffness enhancing mechanism.

According to an exemplary embodiment of the present disclosure, the support structure may be a part of the stator of the magnetic suspension bearing.

According to an exemplary embodiment of the present disclosure, the support structure may be a part of a rotor driver of the magnetic suspension bearing.

According to an exemplary embodiment of the present disclosure, the support structure may be a part of a housing of the magnetic suspension bearing.

According to an exemplary embodiment of the present disclosure, the support structure may also be used to abut the stator permanent magnet of the stiffness enhancing mechanism against a surface of the stator.

According to an exemplary embodiment of the present disclosure, the rotor of the magnetic suspension bearing may be in the shape of a disc.

According to an exemplary embodiment of the present disclosure, an inner peripheral surface of the stator permanent magnet may be aligned with an inner peripheral surface of the stator tooth of the magnetic suspension bearing.

According to an exemplary embodiment of the present disclosure, an outer peripheral surface of the rotor permanent magnet may be aligned with an outer peripheral surface of the rotor of the magnetic suspension bearing.

According to an exemplary embodiment of the present disclosure, the stator teeth may be made of magnetically conductive materials.

According to an exemplary embodiment of the present disclosure, the stator teeth may be made of ferromagnetic materials.

According to an exemplary embodiment of the present disclosure, the rotor may be made of magnetically conductive materials.

According to an exemplary embodiment of the present disclosure, the rotor may be made of ferromagnetic materials.

According to a third aspect of exemplary embodiments of the present disclosure, there is provided a blood pump, which includes the stiffness enhancing mechanism according to the exemplary embodiments of the present disclosure.

According to a fourth aspect of exemplary embodiments of the present disclosure, there is provided a blood pump, which includes the magnetic suspension bearing according to the exemplary embodiments of the present disclosure.

The additional and/or other aspects and advantages of the present disclosure will be set forth in the following description, or may be obvious from the following description or can be learned through the practice of the present invention. The various technical features of the present disclosure can be combined arbitrarily as long as they do not contradict each other.

BRIEF DESCRIPTION OF THE DRAWINGS

With reference to the following detailed description of the specific embodiments of the present disclosure in combination with the accompanying drawings, the above-mentioned features and advantages and other features and advantages of the present disclosure as well as their implementations will become more apparent. In the figures.

Figure 1:
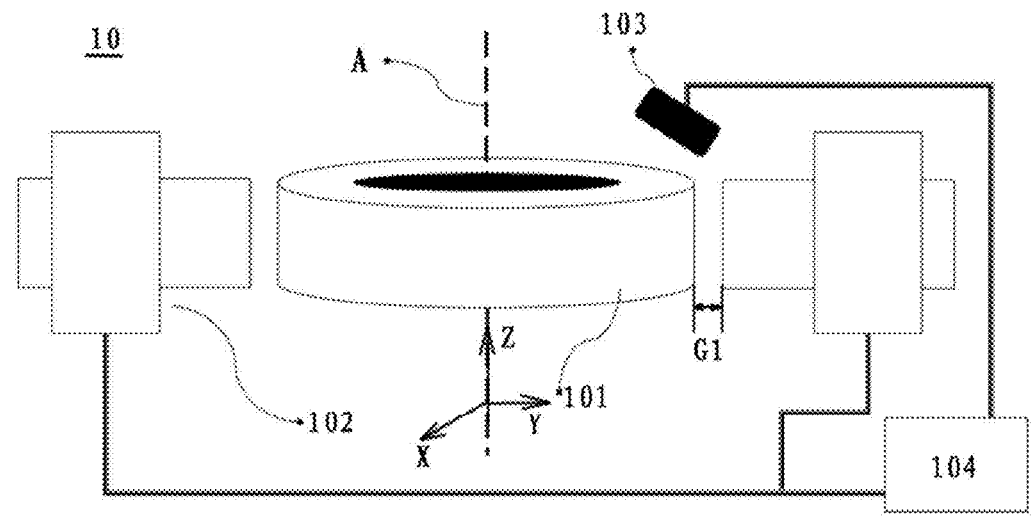
FIG. 1 is a schematic view of a magnetic suspension bearing in the prior art.

In the drawings, respective reference signs indicate respective components. The examples described herein are used to illustrate exemplary aspects of the present invention, and these examples should not be construed as limiting the scope of the present disclosure in any way.

DETAILED EMBODIMENTS

The present disclosure will be described below with reference to the drawings, in which several embodiments of the present disclosure are shown. It should be understood, however, that the present invention may be implemented in many different ways, and is not limited to the embodiments described below. In fact, the embodiments described hereinafter are intended to make a more complete disclosure of the present disclosure and to adequately explain the scope of the present invention to a person skilled in the art. It should also be understood that, the embodiments disclosed herein can be combined in various ways to provide many additional embodiments.

For the purpose of description, the terms "upper", "lower", "left", "right", "vertical", "horizontal", "top", "bottom", "transverse", "perpendicular" and their derivatives are all related to the orientation in the drawings of the present disclosure. However, it should be understood that the present disclosure may adopt various alternative modifications, unless otherwise clearly indicated.

The singular forms "a/an" and "the" as used in the specification, unless clearly indicated, all contain the plural forms. The words "comprising", "containing" and "including" used in the specification indicate the presence of the claimed features, but do not preclude the presence of one or more additional features. The wording "and/or" as used in the specification includes any and all combinations of one or more of the relevant items listed.

In the specification, when an element is referred to as being "on", "attached" to, "connected" to, "coupled" with, "contacting" another element, and so on, it can be directly on, attached to, connected to, coupled with or contacting the other element, or intervening elements may also be present. In contrast, when an element is referred to as being "directly on", "directly attached" to, "directly connected" to, "directly coupled" with or "directly contacting" another element, there are no intervening elements present. In the specification, references to a feature that is disposed "adjacent" another feature may have portions that overlap, overlie or underlie the adjacent feature.

Figure 2:
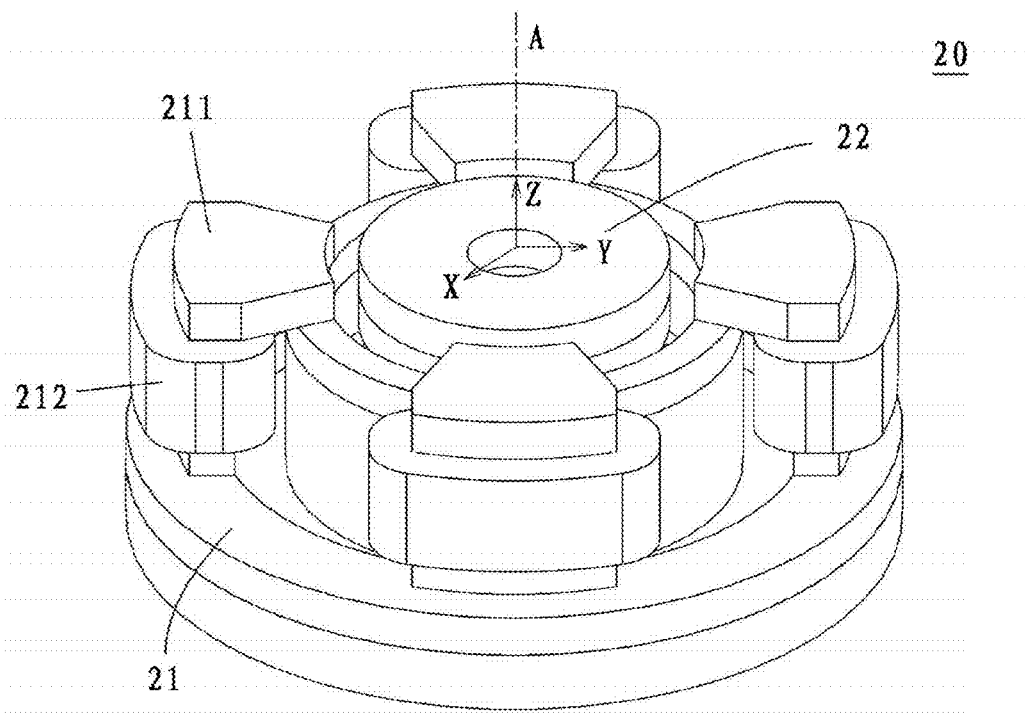
FIG. 2 is a perspective view of a magnetic suspension bearing with a stiffness enhancing mechanism, according to an embodiment of the present disclosure.
Figure 3:
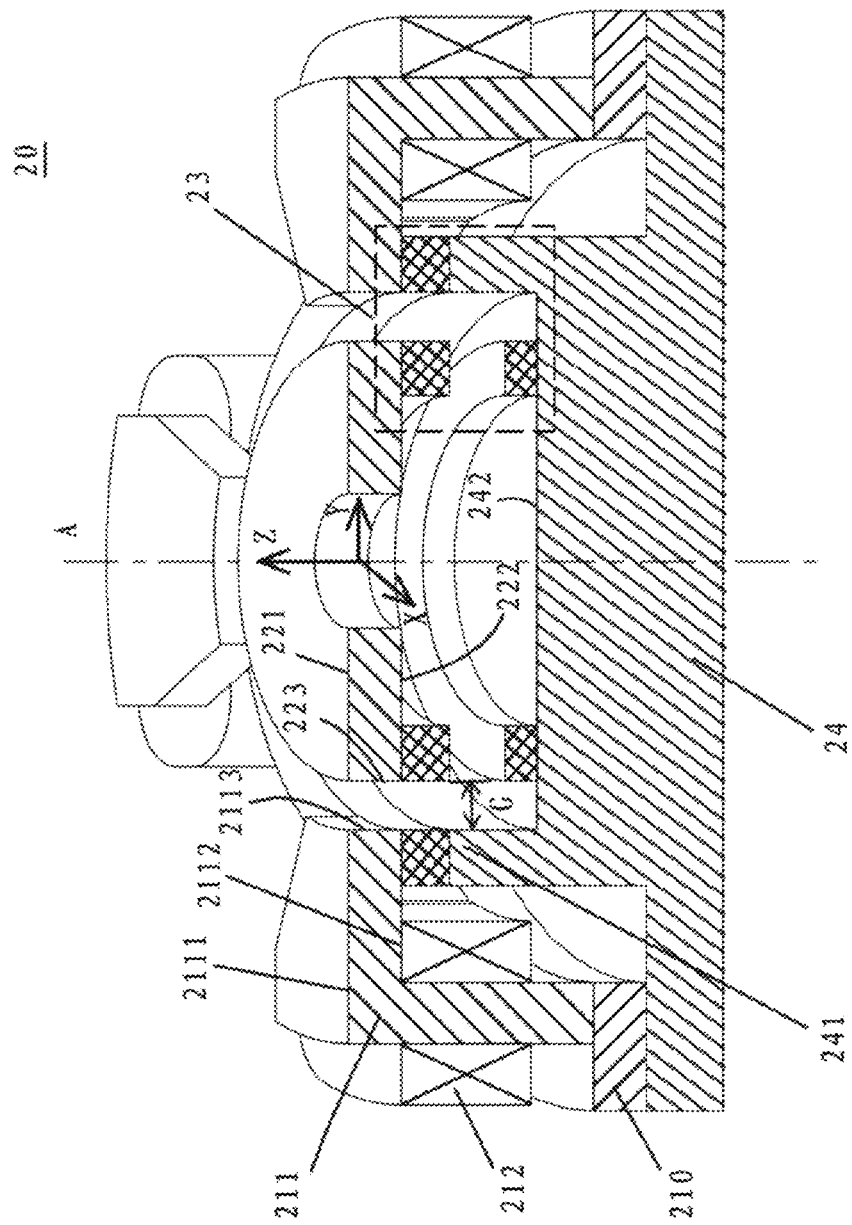
FIG. 3 is a cross-sectional view of the magnetic suspension bearing with the stiffness enhancing mechanism of FIG. 2.

Referring to FIGS. 2 and 3, a magnetic suspension bearing 20 according to an embodiment of the present disclosure is shown. The magnetic suspension bearing 20 includes a stator 21 and a rotor 22 disposed within the stator. The rotor 22 may be in the shape of a disc and is rotatable about an axis of rotation A. Ideally, the stator 21 and the rotor 22 are coaxial. The stator 21 includes a circular stator body 210 and a plurality of stator teeth 211 disposed on the stator body 210 in a circumferential direction. The stator teeth 211 and the rotor 22 are both made of magnetically conductive materials, such as ferromagnetic materials. In the embodiment shown in FIGS. 2 and 3, the stator tooth 211 includes a vertical portion and a horizontal portion that are perpendicular to each other to assume an inverted "L" shape. The horizontal portion of the stator tooth 211 and the rotor 22 may be of the same thickness and may be located at a same height in an ideal situation with a gap or an airgap G existing between the horizontal portion of the stator tooth 211 and the rotor 22. Specifically, the horizontal portion of the stator tooth 211 includes an upper surface 2111, a lower surface 2112, and an arc-shaped inner peripheral surface 2113; the rotor 22 includes an upper surface 221, a lower surface 222, and a circumferential outer peripheral surface 223. Ideally, the upper surfaces 2111 of the horizontal portions of the stator teeth 211 are aligned with the upper surface 221 of the rotor 22, the lower surfaces 2112 of the horizontal portions of the stator teeth 211 are aligned with the lower surface 222 of the rotor 22, and the inner peripheral surfaces 2113 of the horizontal portions of the stator teeth 211 are spaced apart from the outer peripheral surface 223 of the rotor 22 by an equal gap or airgap G. In addition, magnetic suspension coils 212 are wound on the vertical portions of the stator teeth 211 to provide a radial electromagnetic force (attractive force or repulsive force) to the rotor 22, so as to suspend the rotor 22. Specifically, once being excited by current, the magnetic suspension coils 212 can generate an electromagnetic field on the stator teeth 211. By permeation of the magnetic field through the stator teeth 211 and the rotor 22, a radial electromagnetic force (attractive force or repulsive force) can be generated between the stator teeth 211 and the rotor 22 to suspend the rotor 22 in a radial plane (the X-Y plane in FIGS. 2 and 3).

In the embodiment shown in FIGS. 2 and 3, the stator 21 includes four stator teeth 211, each of which is provided with a magnetic suspension coil 212. The four stator teeth 211 are evenly distributed in the circumferential direction, and thus can be divided into two pairs of stator teeth, with the two stator teeth in each pair of stator teeth being arranged opposite to each other in the radial direction. For example, one pair of stator teeth 211 may be disposed oppositely along the X-axis, and the other pair of stator teeth 211 may be disposed oppositely along the Y-axis. More pairs of stator teeth (such as three or four pairs of stator teeth) may also be provided as required without departing from the present disclosure.

According to specific conditions, the magnetic suspension coils 212 on each pair of stator teeth 211 can generate electromagnetic forces in same directions or in opposite directions on the rotor 22. For example, in an ideal condition of the rotor being stably suspended, the magnetic suspension coils 212 on each pair of stator teeth 211 may generate electromagnetic forces in opposite directions on the rotor 22, so that the rotor 22 can be stably suspended in the radial plane without radial displacement along the X-axis or Y-axis. In some cases, for example, when the rotor 22 is radially offset away from a central balanced position due to vibration of the magnetic suspension bearing 20 under the action of external forces, in order to enable the rotor 22 to return to the central balanced position more quickly, the magnetic suspension coils 212 on each pair of stator teeth 211 may generate electromagnetic forces in a same direction on the rotor 22, and the direction of the resultant force of these electromagnetic forces is opposite to the direction in which the rotor is radially offset, thereby helping the rotor 22 to quickly return to the central balanced position. In this case, the magnitude and/or the direction of the electromagnetic forces generated by corresponding one or more magnetic suspension coils 212 can be changed by separately regulating the magnitude and/or the direction of current flowing through said magnetic suspension coils 212, such that the rotor 22 can move oppositely in the radial direction by the generated so-called "push-pull" effect to quickly return to the central balanced position where it can be stably suspended. In the embodiment shown in FIGS. 2 and 3, the magnetic suspension coils 212 on one pair of stator teeth 211 can control displacement of the rotor 22 along the X-axis, and the magnetic suspension coils 212 on the other pair of stator teeth 211 can control displacement of the rotor 22 along the Y-axis, thereby capable of regulating the location of the rotor 22 relative to the stator 21 in the radial plane.

The aforesaid regulation is fulfilled by means of a displacement sensor and a controller. The displacement sensor is used to detect the displacement of the rotor 22 relative to the stator 21 and send a signal to the controller. The controller is connected to the magnetic suspension coils 212 through wires. After receiving a signal from the displacement sensor, the controller separately varies the magnitude and/or the direction of current flowing through corresponding one or more magnetic suspension coils 212 as required, so as to change the magnitude and direction of the resultant force of the radial forces generated between the stator 21 and the rotor 22, such that the rotor can move in a desired direction to achieve regulation of location of the rotor 22 relative to the stator 21 in the radial plane.

As described above, although the magnetic suspension coils 212 arranged in pairs can suspend the rotor 22 in the radial plane, and the location of the rotor 22 relative to the stator 21 in the radial plane can be regulated by using a controller to change the magnitude and the direction of the current flowing through the magnetic suspension coil 212 (that is, the degree of freedom of movement of the rotor 22 along the X-axis and Y-axis is controllable), the degree of freedom of torsion of the rotor 22 cannot be effectively controlled merely by these magnetic suspension coils 212 (i.e. the rotation of the rotor 22 about the X-axis and the Y-axis cannot be effectively controlled).

In order to solve the problem about torsional stiffness of the magnetic suspension bearing and to reduce the volume of the rotor, especially the height of the rotor associated with the secondary flow path as much as possible, the present disclosure proposes a technical solution of adding a stiffness enhancing mechanism 23 (shown by the dashed box in FIG. 3) to the magnetic suspension bearing. The stiffness enhancing mechanism 23 not only significantly increases the torsional stiffness of the rotor of the magnetic suspension bearing (that is, making torsional movement of the rotor less occur), but also eliminates the defects of the prior art structures such as the sandwich structure and significantly reduces the volume of the rotor of the magnetic suspension bearing and the height of the rotor associated with the secondary flow path.

Figure 4:
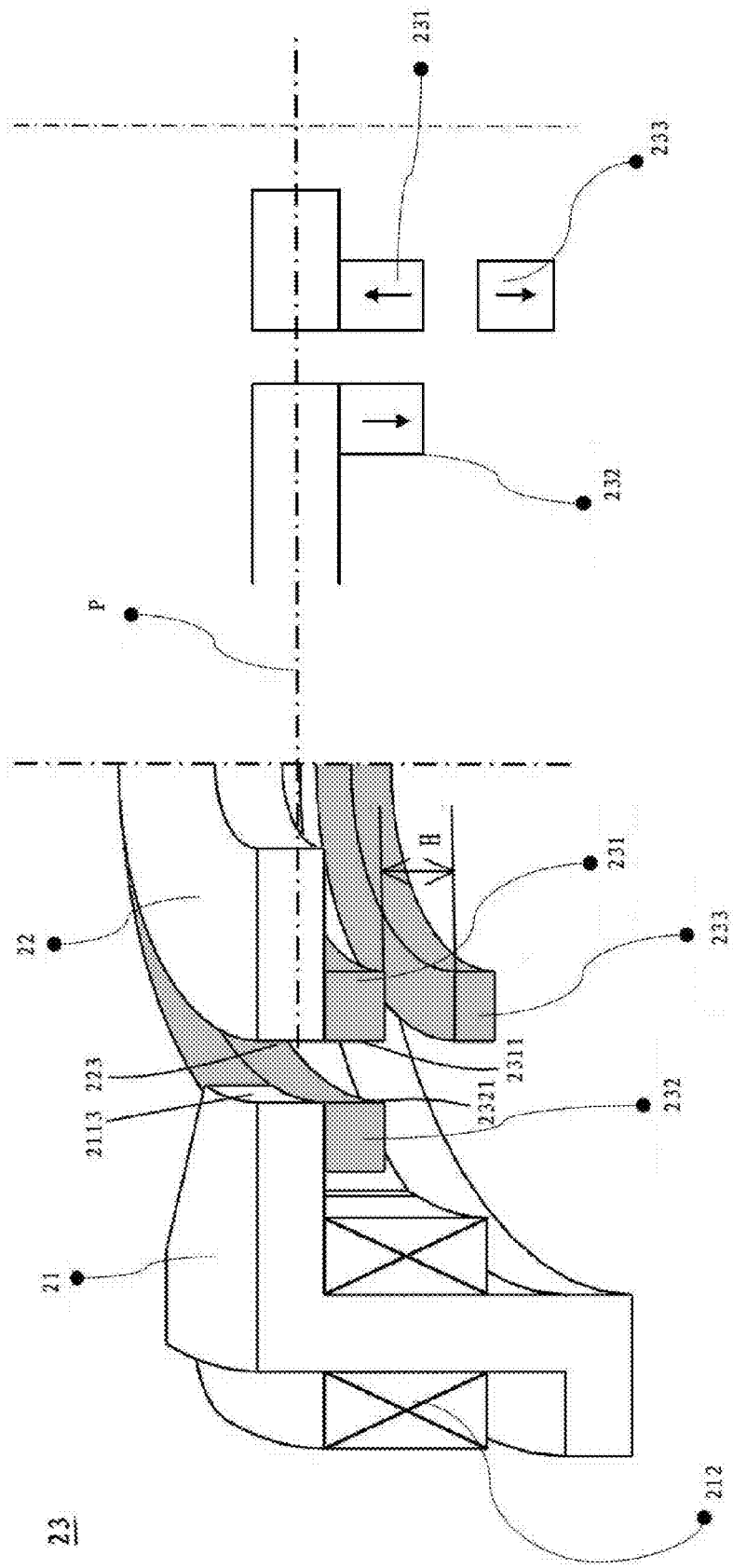
FIG. 4 is a partial perspective view of the stiffness enhancing mechanism of the magnetic suspension bearing of FIG. 2 and schematically shows the magnetization direction of the stiffness enhancing mechanism.
Figure 5:
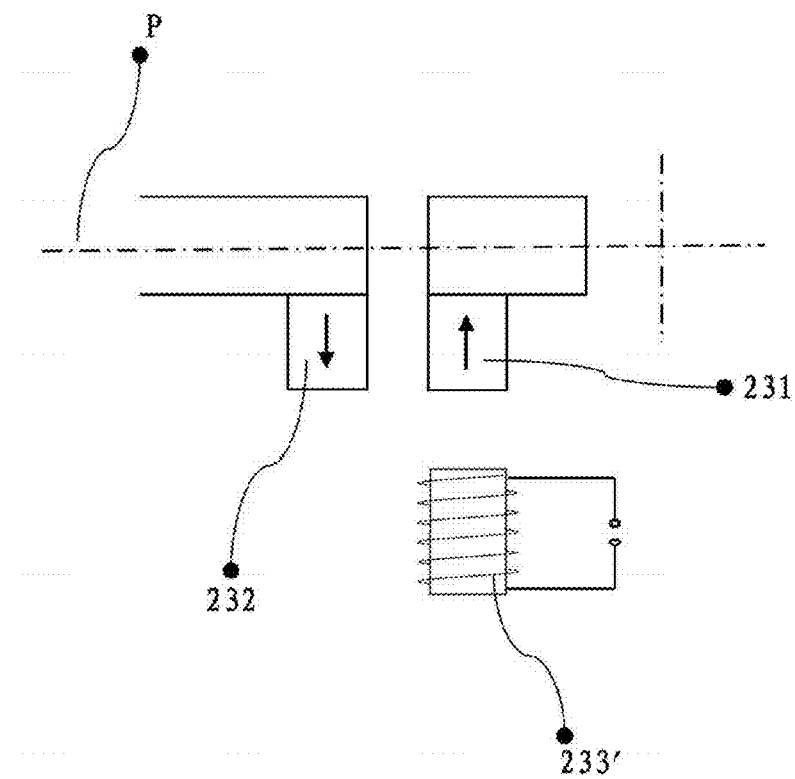
FIG. 5 shows a different embodiment of the axial driving body of the stiffness enhancing mechanism according to the present disclosure.

The specific structure and working principle of the stiffness enhancing mechanism 23 according to the present disclosure will be described in detail with reference to FIGS. 3 to 5, wherein FIG. 3 shows the arrangement of the stiffness enhancing mechanism 23 according to the present disclosure in the magnetic suspension bearing in a cross-sectional view, FIG. 4 more clearly shows the specific structure of the stiffness enhancing mechanism 23 according to the present disclosure in a partial perspective view and shows the magnetization directions of components of the stiffness enhancing mechanism 23 in a schematic view, and FIG. 5 shows a different embodiment of an axial driving body 233 of the stiffness enhancing mechanism 23.

Referring first to FIGS. 3 and 4, the stiffness enhancing mechanism 23 according to the present disclosure includes: a rotor permanent magnet 231 arranged on a side of the rotor 22 with the rotor permanent magnet being parallel to a main plane P of the rotor 22 and abutting against the rotor 22, wherein the main plane P of the rotor is a symmetrical plane of the rotor 22 in the radial direction; a stator permanent magnet 232 arranged on a side of the stator tooth 211 of the stator 21 with the stator permanent magnet being parallel to the main plane P of the rotor 22 and abutting against the stator tooth 211 of the stator 21, wherein the side where the stator permanent magnet 232 is located is the same as the side where the rotor permanent magnet 231 is located, and the stator permanent magnet 232 and the rotor permanent magnet 231 are spaced apart from each other by a certain distance in the radial direction (in the inverted "L"-shaped stator teeth shown in FIGS. 3 and 4, the stator permanent magnet 232 is disposed underneath the horizontal portion of the stator tooth 211 with the stator permanent magnet being parallel to the main plane P of the rotor and abutting against the horizontal portion of the stator tooth 211); and an axial driving body 233 arranged to face the rotor permanent magnet 231 and to be spaced apart from the rotor permanent magnet 231 by a certain distance H in the axial direction (in the embodiment shown in FIGS. 3 and 4, the axial driving body 233 is also parallel to the main plane P of the rotor). In the stiffness enhancing mechanism according to the present disclosure, the rotor permanent magnet 231 and the rotor 22 form a rotor assembly, which has an asymmetric structure with respect to the main plane P of the rotor 22. Further, the stiffness enhancing mechanism according to the present disclosure is configured such that the stator permanent magnet 232 generates a radial attractive force to the rotor permanent magnet 231, and the axial driving body 233 generates an axial repulsive force to the rotor permanent magnet 231, wherein the magnitude of the axial repulsive force is variable with the change of the axial distance between the axial driving body 233 and the rotor permanent magnet 231. The torsional stiffness of the rotor 22 is enhanced through the combined action of the radial attractive force and the axial repulsive force, with its specific principle being described in detail below.

In the embodiment shown in FIGS. 3 and 4, the rotor permanent magnet 231 and the stator permanent magnet 232 are both of an integral structure in circular shape, and both have rectangular cross sections. The rotor permanent magnet 231 may abut against a lower surface 222 of the rotor 22 and the outer peripheral surface 2311 of the rotor permanent magnet 231 may be aligned with the outer peripheral surface 223 of the rotor 22. The stator permanent magnet 232 may abut against a lower surface 2112 of the horizontal portion of the stator tooth 211 and the inner peripheral surface 2321 of the stator permanent magnet 232 may be aligned with the inner peripheral surface 2113 of the horizontal portion of the stator tooth 211. In this way, the rotor permanent magnet 231 and the stator permanent magnet 232 are spaced apart from each other by a same distance as the distance G between the stator 21 and the rotor 22. However, the present disclosure is not limited to this, and the distance at which the rotor permanent magnet 231 and the stator permanent magnet 232 are spaced apart from each other may also be different from the distance G at which the stator 21 and the rotor 22 are spaced apart. In addition, the rotor permanent magnet 231 and the stator permanent magnet 232 may be of the same thickness. However, the present disclosure is not limited to this, and the rotor permanent magnet 231 and the stator permanent magnet 232 may also be of different thicknesses.

The rotor permanent magnet 231 may be fixed to the lower surface 222 of the rotor 22 in various suitable ways. As mentioned above, the rotor assembly formed by the rotor permanent magnet 231 and the rotor 22 has an asymmetric structure with respect to the main plane P of the rotor 22 (that is, the rotor permanent magnet 231 is located only on one side of the main plane P of the rotor 22), which is an important difference from the prior art sandwich structure. The permanent magnets in the prior art structure such as the sandwich structure are usually in symmetrical arrangement relative to the rotor, which necessarily requires at least two permanent magnets to be disposed on both sides of the rotor. Due to the magnetization marginal effect of the permanent magnet as mentioned above, the magnetic field intensity generated by two separate permanent magnets is less than the magnetic field intensity generated by a single permanent magnet of the same volume. Therefore, in case of two permanent magnets being separately disposed, in order to reach a desired magnetic field intensity as that generated by a single permanent magnet, the height or volume of the two permanent magnets must be increased, which is contrary to the current mainstream of seeking miniaturization of the magnetic suspension bearing. The rotor permanent magnet 231 according to the present disclosure is arranged on one side of the rotor 22, and the asymmetric structure formed in this way not only can achieve the same function as the symmetrical structure, but also can reduce the volume of the rotor and the height of the rotor associated with the secondary flow path by adopting a rotor permanent magnet in small volume and height. When such a magnetic suspension bearing is applied to, for example, a blood pump, it can significantly reduce the damage to, for example, blood cells, thereby increasing the blood compatibility.

The axial driving body 233 is located directly below the rotor permanent magnet 231 in the axial direction. Preferably, the axial driving body 233 may be disposed directly below the rotor permanent magnet 231 in a stationary manner. Compared with the way in which the axial driving body 233 is movable, the stationary arrangement of the axial driving body can reduce, to some extent, the adverse effects caused by misalignment of the axial driving body 233 with the rotor permanent magnets 231 due to movement of the axial driving body. However, the present disclosure is not limited to this. The axial driving body 233 may also have a certain degree of freedom, for example, it may also rotate about the axis of rotation A.

In an embodiment according to the present disclosure, the axial driving body 233 may be in the form of a ring-shaped permanent magnet (as shown in FIGS. 3 to 4). The axial driving body 233 in the form of a ring-shaped permanent magnet may have the same width as that of the rotor permanent magnet 231 and may be completely aligned with the rotor permanent magnet 231 in width. However, the present disclosure is not limited to this, and the axial driving body 233 in the form of a ring-shaped permanent magnet may also have a different width from that of the rotor permanent magnet 231. The axial driving body 233 in the form of a ring-shaped permanent magnet forms in space a magnetic field repelling the rotor permanent magnet 231, thereby generating a passive axial repulsive force (i.e., upward thrust force) to the rotor permanent magnet 231. On one hand, when the rotor assembly formed by the rotor permanent magnet 231 and the rotor 22 is horizontally suspended in the radial plane without torsional movement about the X-axis or Y-axis, the passive axial repulsive force tends to push the rotor assembly upward; meanwhile, the rotor assembly undergoes an action of radial attractive force generated by the magnetic suspension coil 212 on the stator 21 and the stator permanent magnet 232, which radial attractive force has a downward pulling force component to resist the passive axial repulsive force generated by the axial driving body 233, such that the rotor assembly is maintained at a desired position in space and can be avoided from colliding with the bottom of the magnetic suspension bearing. On the other hand, when the rotor assembly is tilted in the radial plane and thus has a torsional movement about the X-axis or Y-axis, one end of the rotor permanent magnet 231 will move away from the axial driving body 233 during which the passive axial repulsive force generated by the axial driving body 233 to this end of the rotor permanent magnet 231 will be reduced, and the other end of the rotor permanent magnet 231 will approach the axial driving body 233 during which the passive axial repulsive force generated by the axial driving body 233 to this end of the rotor permanent magnet 231 will be increased. As the passive axial repulsive forces applied by the axial driving body 233 to the two ends of the rotor permanent magnet 231 are not equal, a net torque about the X axis or the Y axis is generated on the rotor permanent magnet 231. The net torque is opposite to the torsion direction of the rotor assembly, thereby resisting the torsion of the rotor assembly and returning the rotor assembly to the radial plane. In other words, in the process that different portions of the rotor assembly move up and down due to the torsional movement of the rotor assembly, the axial driving body 233 generates passive axial repulsive forces of different magnitudes according to the distances from the different portions of the rotor assembly. These passive axial repulsive forces of different magnitudes produce a net torque against torsion of the rotor assembly on the rotor permanent magnet 231 and the rotor assembly. This net torque, together with the radial attractive force generated by the stator, acts on the rotor assembly to make the rotor assembly return to and stably suspended in the radial plane. This increases the torsional stiffness of the rotor assembly as a whole, i.e. producing an effect of stiffness enhancing. It is to be noted that this regulation process of the stiffness enhancing mechanism 23 is a dynamic balancing process.

In another embodiment according to the present disclosure, the axial driving body may be in the form of an electromagnet or an air coil 233' (as shown in FIG. 5). In the embodiment where the electromagnet or air coil 233' is used as the axial driving body, the axial driving body may include multiple electromagnets or air coils (only one electromagnet or air coil is shown in FIG. 5), preferably multiple electromagnets or air coils in pairs. These electromagnets or air coils may be disposed directly below the rotor permanent magnet 231 at a distance, preferably at an even distance, from each other in the circumferential direction. The axial driving body in the form of an electromagnet or an air coil 233' is actively controllable, that is, the magnitude and the direction of the current flowing through each electromagnet or air coil can be separately changed by a controller or a control circuit. In this way, if required, the controller or control circuit may be used to change the magnitude and the direction of the current flowing through any corresponding one or more electromagnets or air coils so as to change the magnitude or nature of the electromagnetic force generated by the corresponding one or more electromagnets or air coils (that is, capable of changing the magnitude of the axial repulsive force generated by the axial driving body, and capable of changing the initial axial repulsive force generated by the axial driving body into an axial attractive force), thereby increasing the torsional stiffness of the rotor assembly.

Specifically, when the rotor assembly formed by the rotor permanent magnets 231 and the rotor 22 has one end close to the axial driving body and its opposite end away from the axial driving body due to torsional movement (that is, rotating about the X-axis or Y-axis), the magnitude and/or the direction of the current flowing through the electromagnets or air coils corresponding to the two ends can be changed, so that the corresponding electromagnets or air coils together generate a net torque against the torsion of the rotor assembly to return the rotor assembly to the radial plane. In particular, it is possible to only change the magnitude of the current flowing through the electromagnets or air coils corresponding to the two ends, for example, increase the current flowing through the electromagnet or air coil close to the rotor assembly to generate a greater thrust force to the rotor assembly, and meanwhile reduce the current flowing through the electromagnet or air coil far away from the rotor assembly to generate a smaller thrust force to the rotor assembly, thereby forming a greater net torque on the rotor assembly to quickly return the rotor assembly to the radial plane. It is also possible to change only the direction of current flowing through the electromagnet or air coil corresponding to one of the two ends, for example, to keep the direction of the current flowing through the electromagnet or air coil close to the rotor assembly unchanged so that an axial repulsion (thrust) force is continued to be generated to the rotor assembly, and to change the direction of the current flowing through the electromagnet or air coil away from the rotor assembly so that an axial attractive force is generated to the rotor assembly. By this way of pushing at one end and attracting at the other end, a greater net torque is formed on the rotor assembly to enable the rotor assembly to quickly return to the radial plane. It is also possible to combine the previous two regulations methods by simultaneously changing the magnitude and the direction of the current flowing through the electromagnets or air coils corresponding to the two ends to obtain a greater net torque, so that the rotor assembly can return to the radial plane more quickly.

Compared with the use of permanent magnets as the axial driving body, the use of electromagnets or air coils 233' as the axial driving body can increase the torsional stiffness of the rotor assembly more significantly and enable the rotor assembly to be suspended more stably. However, in the case of using the electromagnet or air coil as the axial driving body, the electromagnet or air coil requires a large volume and a complicated control circuit. Therefore, if it is required to miniaturize the entire magnetic suspension bearing, the use of the permanent magnets as the axial driving body will be a better choice; but if it is only required to miniaturize the rotor itself (for example, the magnetic suspension bearing is configured as a component placed outside the human body), the use of an actively controllable electromagnet or air coil will be the better choice.

FIGS. 4 and 5 also show the magnetization directions of the rotor permanent magnet 231 and the stator permanent magnet 232, in which mono-magnetization directions are shown. Specifically, the rotor permanent magnet 231 and the stator permanent magnet 232 shown in FIGS. 4 and 5 have axially-magnetized mono-magnetization directions. However, the present disclosure is not limited to this. As long as a radial attractive force required by the present disclosure can be generated between the rotor permanent magnet 231 and the stator permanent magnet 232, the rotor permanent magnet 231 and the stator permanent magnet 232 may have any other forms of mono-magnetization directions (such as radially-magnetized or other suitable forms of mono-magnetization directions), and the rotor permanent magnet 231 and the stator permanent magnet 232 may have mono-magnetization directions in different magnetization directions (for example, the rotor permanent magnet 231 has an axial magnetization direction while the stator permanent magnet 232 has a radial magnetization direction, etc.). In addition, the rotor permanent magnet 231 and the stator permanent magnet 232 may also have non-single magnetization directions, such as tapered magnetization directions or other known or unknown non-single magnetization directions, as long as a radial attractive force can be generated between the rotor permanent magnet 231 and the stator permanent magnet 232.

Returning to FIG. 3, the magnetic suspension bearing 20 further includes a support structure 24, which may be used to support the axial driving body 233 of the stiffness enhancing mechanism 23. In the embodiment shown in FIG. 3, the support structure 24 is used to support the stator 21, the stator permanent magnet 232, and the axial driving body 233 at the same time. In this exemplary embodiment, a central portion of the support structure 24 includes a boss, which includes a circular flange 241 and a cavity 242 surrounded by the circular flange. The circular flange 241 is used to support the stator permanent magnet 232 and abut the stator permanent magnet 232 against the lower surface 2112 of the horizontal portion of the stator teeth 211. The axial driving body 233 is placed on the bottom of the cavity 242 of the boss. Preferably, the axial driving body 233 is placed on the bottom of the cavity 242 of the boss in a stationary manner.

The support structure 24 may be a part of the stator 21. However, the present disclosure is not limited to this. The support structure 24 may be a part of a housing of the magnetic suspension bearing 20, or a part of other suitable components of the magnetic suspension bearing 20, such as a part of a rotor driver (for example, a driving motor) of the magnetic suspension bearing 20.

Figure 6:
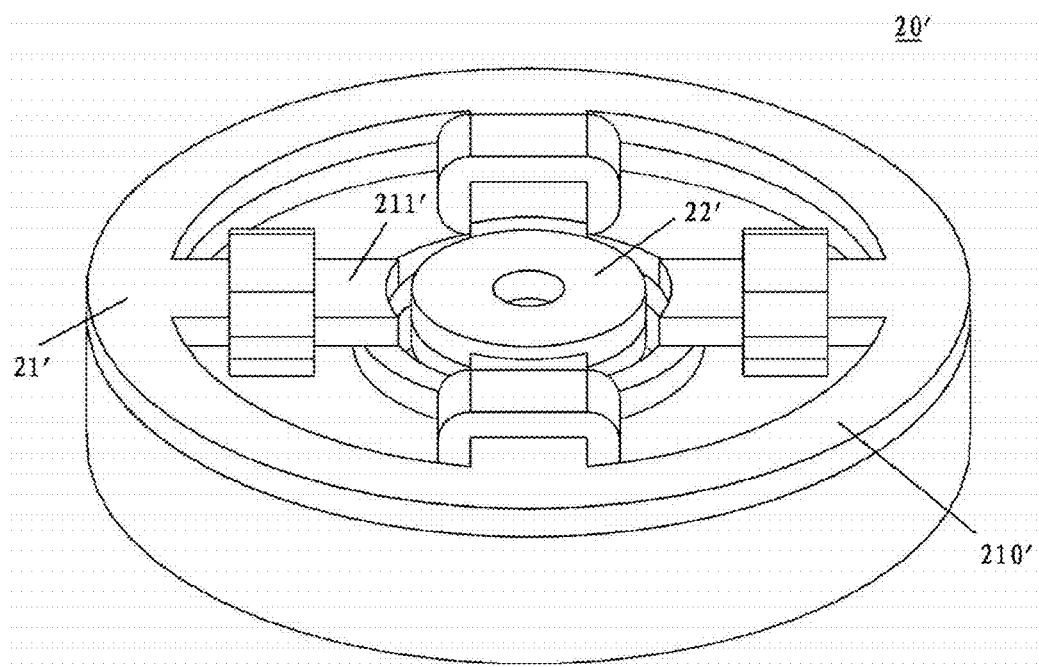
FIG. 6 is a perspective view of a magnetic suspension bearing with a stiffness enhancing mechanism, according to another embodiment of the present disclosure.
Figure 7:
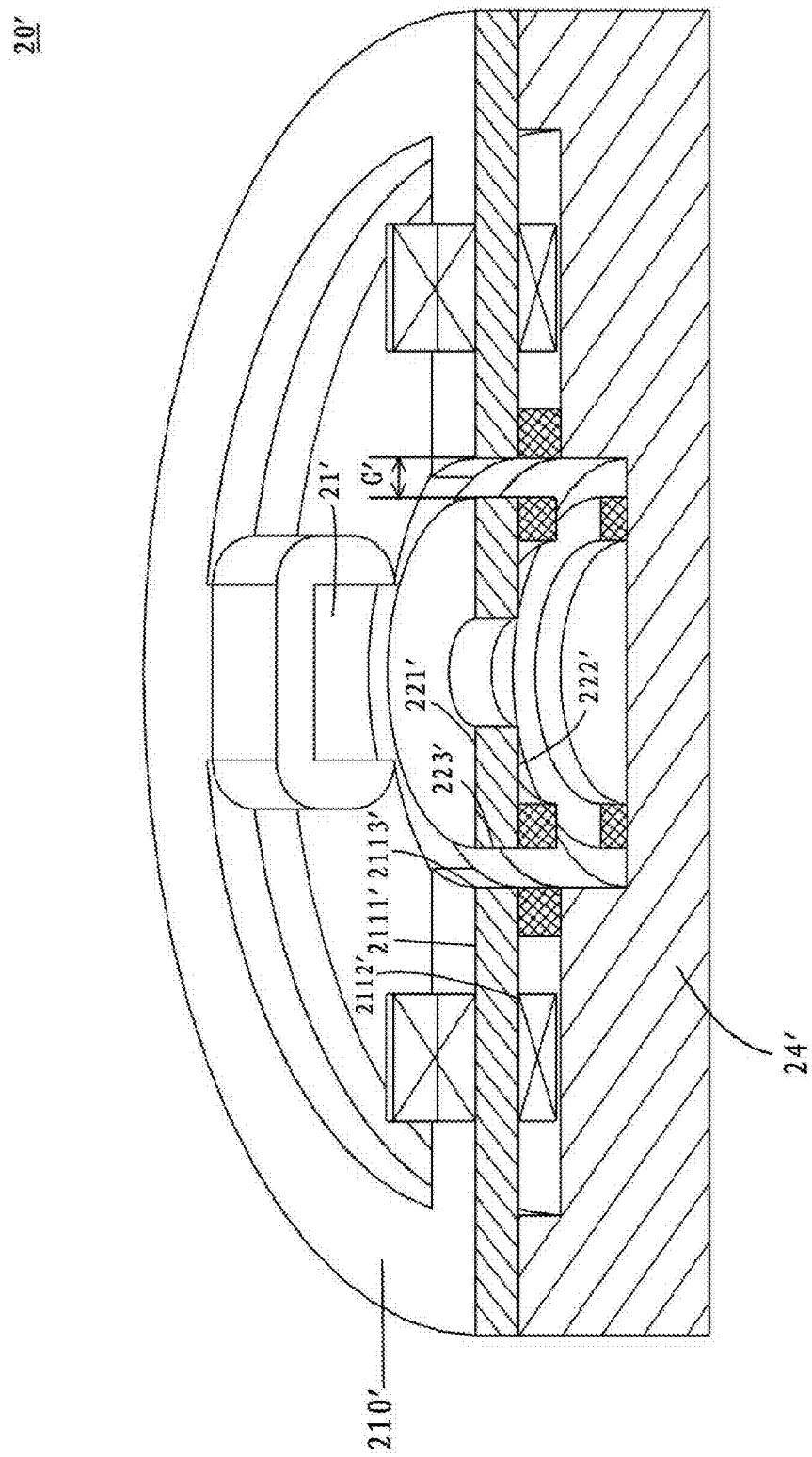
FIG. 7 is a cross-sectional view of the magnetic suspension bearing with the stiffness enhancing mechanism of FIG. 6.

Refer next to FIGS. 6 and 7, which are a perspective view and a cross-sectional view of the magnetic suspension bearing 20' according to another embodiment of the present disclosure respectively. The magnetic suspension bearing 20' shown in FIGS. 6 and 7 has a similar structure to the magnetic suspension bearing 20 shown in FIGS. 2 and 3, only with differences in the stator teeth and the support structure. Therefore, for the sake of simplicity, only the different parts will be described with the same components being omitted.

In the embodiment shown in FIGS. 6 and 7, the stator 21' includes a circular stator body 210' and four linearly-shaped stator teeth 211'. The four linearly-shaped stator teeth 211' are evenly disposed along the circumferential direction, and extend from the stator body 210' toward a center of the stator along the radial direction. Each linearly-shaped stator tooth 211' may have a uniform width (as shown in FIGS. 6 and 7), but it may also have a non-uniform width, for example, the stator tooth 211' may have a tapered width, or the like.

Likewise, the rotor 22' may be in the shape of a disc, and there is a gap or airgap G' between the stator teeth 211' and the rotor 22'. The stator teeth 211' and the rotor 22' may be of the same thickness, and are ideally located at a same height. In other words, ideally, upper surfaces 2111' of the stator teeth 211' are aligned with an upper surface 221' of the rotor 22', lower surfaces 2112' of the stator teeth 211' are aligned with a lower surface 222' of the rotor 22', and inner peripheral surfaces 2113' of the stator teeth 211 are spaced apart from an outer peripheral surface 223' of the rotor 22' by an equal gap or airgap G'.

The stiffness enhancing mechanism of the magnetic suspension bearing 20' shown in FIGS. 6 and 7 is the same in structure and arrangement as the stiffness enhancing mechanism of the magnetic suspension bearing 20 shown in FIGS. 2 and 3, which will not be repeated here. The magnetic suspension bearing 20' also includes a support structure 24', which is also used to support the stator, the stator permanent magnet, and the axial driving body. Different from the structure shown in FIG. 3, the support structure 24' shown in FIG. 7 has a stepped shape, with its height gradually decreasing from the outer periphery to the center, thereby forming a cavity in the center. The outermost step of the support structure 24' is used to support the stator body 210', the intermediate step is used to support the stator permanent magnets and abut the stator permanents magnet against the lower surface 2112' of the stator teeth 211', and the axial driving body is placed on the bottom of the cavity in the center of the support structure 24'.

Likewise, the support structure 24' may be a part of the stator 21'. However, the present disclosure is not limited to this. The support structure 24' may also be a part of a housing of the magnetic suspension bearing 20', or a part of other suitable components of the magnetic suspension bearing 20', such as a part of a rotor driver (for example, a driving motor) of the magnetic suspension bearing 20'.

Although the exemplary embodiments of the present disclosure have been described above with reference to FIGS. 1 to 7, those skilled in the art should understand that the present disclosure is not limited to the specific structure that has been disclosed. Multiple changes and modifications may be made to the exemplary embodiments without substantively departing from the spirit and scope of the present invention. Accordingly, all the changes and modifications are encompassed within the protection scope of the present invention as defined by the claims.

For example, the magnetization directions of the rotor permanent magnet, the stator permanent magnet, and the axial driving body shown in FIG. 4 are just an example. Any permanent magnet magnetization directions that can generate a radial attractive force between the rotor and the stator and an axial repulsive force between the rotor and the axial driving body all conform to the principle of the present invention.

For another example, in the magnetic suspension bearings shown in FIGS. 2-3 and 6-7, the rotor permanent magnet, the stator permanent magnet, and the axial driving body that is configured by a permanent magnet are all shown as an integral structure in a circular shape. However, the present invention is not limited to this. One or all of the rotor permanent magnet, the stator permanent magnet, and the axial driving body may be composed of a plurality of discrete permanent magnets spaced apart in the circumferential direction, as long as the desired stiffness enhancing effect can be reached. The plurality of the discrete permanent magnets may be arc-shaped. The use of a plurality of spaced-apart discrete permanent magnets can, for example, reduce the total mass of the permanent magnets to some extent, which is advantageous in applications where a higher requirement of the total mass is needed. However, when the plurality of spaced-apart discrete permanent magnets are used as the rotor permanent magnet, the stator permanent magnet or the axial driving body, uneven magnetic force may be generated in the circumferential direction due to discontinuity of the discrete permanent magnets in the circumferential direction. This may cause vibration of the rotor, and accordingly may affect the suspension stability of the rotor to some extent.

For another example, in the magnetic suspension bearings shown in FIGS. 2-3 and 6-7, the support structure is shown to simultaneously support the stator, the stator permanent magnet, and the axial driving body. However, the present disclosure is not limited to this. The support structure is mainly used to support the axial driving body, and the stator and the stator permanent magnet may be supported by other suitable components. Further, in the magnetic suspension bearings shown in FIGS. 2-3 and 6-7, the support structure is shown as an integral structure. However, the present disclosure is not limited to this, and the support structure may be assembled from multiple components.

The present disclosure is defined by the appended claims, and equivalents of these claims are also included in the scope of the present disclosure.

What is claimed is:

1. A stiffness enhancing mechanism for an active magnetic suspension bearing, wherein the active magnetic suspension bearing comprises a stator, and a rotor disposed within the stator, wherein the rotor comprises an upper surface and a lower surface that are perpendicular to an axis of rotation and a circumferential outer peripheral surface that is around the axis of rotation and wherein the rotor is rotatable about the axis of rotation, and the stator comprises a plurality of stator teeth spaced apart from each other in a circumferential direction, wherein each stator tooth of the plurality of stator teeth comprises a magnetic suspension coil for suspending the rotor and controlling the movement of the rotor in a radial direction, and a gap exists between each stator tooth and the rotor, and wherein the stiffness enhancing mechanism is configured to control a degree of freedom of torsion about the radial direction of the rotor and comprises:

a rotor permanent magnet fixed to the lower surface of the rotor that is perpendicular to the axis of rotation, wherein the rotor permanent magnet is parallel to a main plane of the rotor and abuts against the rotor, wherein the main plane of the rotor is a plane of symmetry of the rotor that extends perpendicular to the axis of rotation of the rotor;

a stator permanent magnet arranged underneath horizontal portions of the plurality of stator teeth of the stator and on lower surfaces of the horizontal portions of the plurality of stator teeth of the stator, wherein the stator permanent magnet is parallel to the main plane of the rotor and abuts against the stator teeth of the stator, wherein a side where the stator permanent magnet is located is the same as a side where the rotor permanent magnet is located, and the stator permanent magnet is spaced apart from the rotor permanent magnet by a distance in the radial direction; and an axial driving body arranged to face the rotor permanent magnet and spaced apart from the rotor permanent magnet by a distance in an axial direction;

wherein the rotor permanent magnet and the rotor form a rotor assembly, and the rotor assembly has an asymmetric structure with respect to the main plane of the rotor;

wherein the stiffness enhancing mechanism is configured such that the stator permanent magnet generates a radial attractive force to the rotor permanent magnet and the axial driving body generates an axial repulsive force to the rotor permanent magnet, wherein a torsional stiffness of the rotor is enhanced through a combined action of the radial attractive force and the axial repulsive force, and wherein a magnitude of the axial repulsive force is capable of decreasing when an axial distance between the axial driving body and the rotor permanent magnet increases, and the magnitude of the axial repulsive force is capable of increasing when the axial distance between the axial driving body and the rotor permanent magnet decreases.

2. The stiffness enhancing mechanism according to claim 1, wherein the rotor permanent magnet has a mono-magnetization direction which is an axial magnetization direction or a radial magnetization direction, and/or the stator permanent magnet has a mono-magnetization direction which is an axial magnetization direction or a radial magnetization direction.

3. The stiffness enhancing mechanism according to claim 1, wherein the rotor permanent magnet is of an integral structure in a circular shape or composed of a plurality of discrete permanent magnets spaced apart from each other in a circumferential direction, and/or the stator permanent magnet is of an integral structure in a circular shape or composed of a plurality of discrete permanent magnets spaced apart from each other in a circumferential direction.

4. The stiffness enhancing mechanism according to claim 1, wherein the axial driving body is configured to be stationary.

5. The stiffness enhancing mechanism according to claim 1, wherein the axial driving body comprises at least one of a permanent magnet having an integral structure in a circular shape, or a plurality of discrete permanent magnets spaced apart from each other in a circumferential direction.

6. The stiffness enhancing mechanism according to claim 1, wherein the axial driving body comprises at least one of an electromagnet or an air coil.

7. The stiffness enhancing mechanism according to claim 6, wherein the axial driving body comprises at least one of a plurality of electromagnets or a plurality of air coils spaced apart from each other in a circumferential direction.

8. The stiffness enhancing mechanism according to claim 7, wherein the stiffness enhancing mechanism further includes a controller or a control circuit capable of separately varying a magnitude of current flowing through each electromagnet or air coil, so as to separately change a magnitude of the axial repulsive force generated by corresponding one or more electromagnets or air coils to the rotor permanent magnet.

9. The stiffness enhancing mechanism according to claim 8, wherein when a torsional movement about the radial direction occurs to the rotor, the controller or the control circuit of the stiffness enhancing mechanism reduces a current flowing through one or more electromagnets or air coils corresponding to an end of the rotor permanent magnet that moves away from the axial driving body and meanwhile increases a current flowing through one or more electromagnets or air coils corresponding to the other end of the rotor permanent magnet that approaches the axial driving body.

10. The stiffness enhancing mechanism according to claim 8, wherein the controller or control circuit of the stiffness enhancing mechanism is also capable of separately changing direction of a current flowing through each electromagnet or air coil, and when a torsional movement about the radial direction occurs to the rotor, the controller or the control circuit of the stiffness enhancing mechanism changes a direction of current flowing through one or more electromagnets or air coils corresponding to an end of the rotor permanent magnet that moves away from the axial driving body, so as to change the axial repulsive force generated by the one or more electromagnets or air coils to the rotor permanent magnet into an axial attractive force.

11. An active magnetic suspension bearing comprising a stiffness enhancing mechanism, a stator, and a rotor disposed within the stator, wherein the rotor comprises an upper surface and a lower surface that are perpendicular to an axis of rotation and a circumferential outer peripheral surface that is around the axis of rotation, and wherein the rotor is rotatable about the axis of rotation and the stator comprises a plurality of stator teeth spaced apart from each other in a circumferential direction, wherein each stator tooth of the plurality of stator teeth is provided with a magnetic suspension coil for suspending the rotor and controlling the movement of the rotor in a radial direction, and a gap exists between each stator tooth and the rotor, and wherein the stiffness enhancing mechanism is configured to control a degree of freedom of torsion about the radial direction of the rotor and comprises:

a rotor permanent magnet fixed to the lower surface of the rotor that is perpendicular to the axis of rotation, wherein the rotor permanent magnet is parallel to a main plane of the rotor and abuts against the rotor, wherein the main plane of the rotor is a plane of symmetry of the rotor that extends perpendicular to the axis of rotation of the rotor;

a stator permanent magnet arranged underneath horizontal portions of the plurality of stator teeth of the stator and on lower surfaces of the horizontal portions of the plurality of stator teeth of the stator, wherein the stator permanent magnet is parallel to the main plane of the rotor and abuts against the stator teeth of the stator, wherein a side where the stator permanent magnet is located is the same as a side where the rotor permanent magnet is located, and the stator permanent magnet is spaced apart from the rotor permanent magnet by a distance in the radial direction; and an axial driving body arranged to face the rotor permanent magnet and be spaced apart from the rotor permanent magnet by a distance in an axial direction;

wherein the rotor permanent magnet and the rotor form a rotor assembly, and the rotor assembly has an asymmetric structure with respect to the main plane of the rotor;

wherein the stiffness enhancing mechanism is configured such that the stator permanent magnet generates a radial attractive force to the rotor permanent magnet and the axial driving body generates an axial repulsive force to the rotor permanent magnet, wherein a torsional stiffness of the rotor is enhanced through a combined action of the radial attractive force and the axial repulsive force, and wherein a magnitude of the axial repulsive force is capable of decreasing when an axial distance between the axial driving body and the rotor permanent magnet increases, and the magnitude of the axial repulsive force is capable of increasing when the axial distance between the axial driving body and the rotor permanent magnet decreases.

12. The active magnetic suspension bearing according to claim 11, wherein each stator tooth of the plurality of stator teeth includes a horizontal portion and a vertical portion to assume an inverted "L" shape, the horizontal portion of each stator tooth and the rotor are located at a substantially same height with the gap existing between the horizontal portion of the stator tooth and the rotor, the magnetic suspension coil is wound on the vertical portion of the stator tooth, and a magnetic flux generated by the magnetic suspension coil is capable of passing through the horizontal portion of the stator tooth, through the gap between the horizontal portion of the stator tooth and the rotor, and through the rotor; or each stator tooth of the plurality of stator teeth extends from a stator body towards the center in the radial direction to assume a linear shape, each stator tooth and the rotor are located at a substantially same height with the gap existing between the stator tooth and the rotor, the magnetic suspension coil is wound on the stator tooth, and a magnetic flux generated by the magnetic suspension coil is capable of passing through the stator tooth, through the gap between the stator tooth and the rotor, and through the rotor.

13. The active magnetic suspension bearing according to claim 11, wherein the active magnetic suspension bearing further comprises a displacement sensor and a controller, wherein the displacement sensor is used to measure a displacement of the rotor in the radial direction and send a displacement signal to the controller of the active magnetic suspension bearing, and the controller of the active magnetic suspension bearing is used to separately change a magnitude and/or a direction of current flowing through corresponding one or more magnetic suspension coils based on the displacement signal to thereby control movement of the rotor in the radial direction.

14. The active magnetic suspension bearing according to claim 11, wherein the active magnetic suspension bearing further comprises a support structure for supporting the axial driving body and/or for abutting the stator permanent magnet against the lower surfaces of the plurality of stator teeth of the stator;
wherein the support structure is a part of at least one of the stator of the active magnetic suspension bearing, a rotor driver of the magnetic suspension bearing, or a housing of the active magnetic suspension bearing.

15. The active magnetic suspension bearing according to claim 11, wherein the rotor is in the shape of a disc; and/or an inner peripheral surface of the stator permanent magnet is aligned with an inner peripheral surface of each stator tooth of the plurality of stator teeth; and/or
an outer peripheral surface of the rotor permanent magnet is aligned with an outer peripheral surface of the rotor of the active magnetic suspension bearing.

16. The active magnetic suspension bearing according to claim 11, wherein the plurality of stator teeth and/or the rotor comprises magnetically conductive materials.

17. The active magnetic suspension bearing according to claim 16, wherein the plurality of stator teeth and/or the rotor comprises ferromagnetic materials.

18. A blood pump comprising an active magnetic suspension bearing, wherein the active magnetic suspension bearing comprises a stiffness enhancing mechanism, a stator, and a rotor disposed within the stator, wherein the rotor comprises an upper surface and a lower surface that are perpendicular to an axis of rotation and a circumferential outer peripheral surface that is around the axis of rotation, and wherein the rotor is rotatable about the axis of rotation and the stator comprises a plurality of stator teeth spaced apart from each other in a circumferential direction, wherein each stator tooth of the plurality of stator teeth is provided with a magnetic suspension coil for suspending the rotor and controlling the movement of the rotor in a radial direction, and a gap exists between each stator tooth and the rotor, and wherein the stiffness enhancing mechanism is configured to control a degree of freedom of torsion about the radial direction of the rotor and comprises:
a rotor permanent magnet fixed to the lower surface of the rotor that is perpendicular to the axis of rotation, wherein the rotor permanent magnet is parallel to a main plane of the rotor and abuts against the rotor, wherein the main plane of the rotor is a plane of symmetry of the rotor that extends perpendicular to the axis of rotation of the rotor;
a stator permanent magnet arranged underneath horizontal portions of the plurality of stator teeth of the stator and on lower surfaces of the horizontal portions of the plurality of the stator teeth of the stator, wherein the stator permanent magnet is parallel to the main plane of the rotor and abuts against the stator teeth of the stator, wherein a side where the stator permanent magnet is located is the same as a side where the rotor permanent magnet is located, and the stator permanent magnet is spaced apart from the rotor permanent magnet by a distance in the radial direction; and
an axial driving body arranged to face the rotor permanent magnet and be spaced apart from the rotor permanent magnet by a distance in an axial direction;
wherein the rotor permanent magnet and the rotor form a rotor assembly, and the rotor assembly has an asymmetric structure with respect to the main plane of the rotor;
wherein the stiffness enhancing mechanism is configured such that the stator permanent magnet generates a radial attractive force to the rotor permanent magnet and the axial driving body generates an axial repulsive force to the rotor permanent magnet, wherein a torsional stiffness of the rotor is enhanced through a combined action of the radial attractive force and the axial repulsive force, and wherein a magnitude of the axial repulsive force is capable of decreasing when an axial distance between the axial driving body and the rotor permanent magnet increases, and the magnitude of the axial repulsive force is capable of increasing when the axial distance between the axial driving body and the rotor permanent magnet decreases.

* * * * *